United States Patent [19]

Takao

[11] Patent Number: 4,532,339

[45] Date of Patent: Jul. 30, 1985

[54] PROCESS FOR PURIFYING AMINOSULFENYLCARBAMATE DERIVATIVES

[75] Inventor: Hisashi Takao, Tokushima, Japan

[73] Assignee: Otsuka Kagaku Yakuhin Kabushiki Kaisha, Osaka, Japan

[21] Appl. No.: 585,462

[22] Filed: Mar. 2, 1984

[51] Int. Cl.³ ............... C07D 307/86; C07C 161/00
[52] U.S. Cl. .................. 549/470; 544/58.1; 544/58.7; 544/153; 544/158; 546/196; 546/247; 548/525; 548/542; 260/453.3
[58] Field of Search .......... 549/470; 260/453.3

[56] References Cited

U.S. PATENT DOCUMENTS 4,006,231 2/1977 Black et al. ............... 424/248.5
4,329,293 5/1982 Ager et al. ................ 549/470

OTHER PUBLICATIONS

Rizzo, Chem. Abstracts, 6344d, Ger. Offen. 2655212, (1977).

Primary Examiner—Henry R. Jiles
Assistant Examiner—Bernard I. Dentz
Attorney, Agent, or Firm—Armstrong, Nikaido, Marmelstein & Kubovcik

[57] ABSTRACT

A process for purifying an aminosulfenylcarbamate derivative represented by the formula (I)

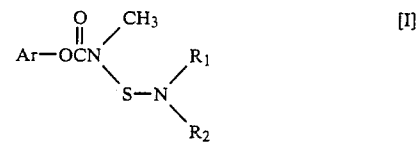

wherein Ar is

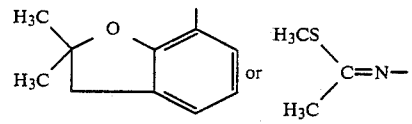

and $R^1$ and $R^2$ are the same or different and are each $C_{1-8}$ alkyl, $C_{3-6}$ cycloalkyl, benzyl which is unsubstituted or substituted with halogen, $C_{1-3}$ alkyl or $C_{1-3}$ alkoxy, phenyl which is unsubstituted or substituted with halogen, $C_{1-3}$ alkyl or $C_{1-3}$ alkoxy, —X—COOR³ or —Y—CN (in which X and Y are each straight-chain or branched-chain alkylene and $R^3$ is $C_{1-8}$ alkyl or $C_{3-6}$ cycloalkyl), $R^1$ and $R^2$, when taken together, represent a 5- or 6-membered heterocyclic ring which may contain a sulphur or oxygen atom, the process comprising bringing a solution of the unreacted carbamate-containing aminosulfenylcarbamate derivative of the formula (I) in a water-insoluble organic solvent into contact with an aqueous alkali solution or a mixture of alkali, water and a water-soluble organic solvent. The aminosulfenylcarbamate derivatives are known insecticides.

7 Claims, No Drawings

PROCESS FOR PURIFYING AMINOSULFENYLCARBAMATE DERIVATIVES

This invention relates to a process for purifying aminosulfenylcarbamate derivatives.

Aminosulfenylcarbamate derivatives represented by the formula

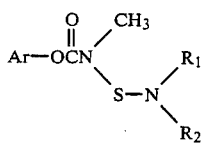

wherein Ar is

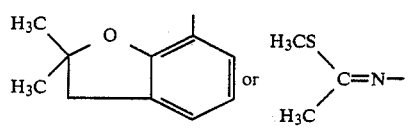

and $R^1$ and $R^2$ are the same or different and are each $C_{1-8}$ alkyl, $C_{3-6}$ cycloalkyl, benzyl which is unsubstituted or substituted with halogen, $C_{1-3}$ alkyl or $C_{1-3}$ alkoxy, phenyl which is unsubstituted or substituted with halogen, $C_{1-3}$ alkyl or $C_{1-3}$ alkoxy, —X—COOR$^3$ or —Y—CN (in which X and Y are each straight-chain or branched-chain alkylene and $R^3$ is $C_{1-8}$ alkyl or $C_{3-6}$ cycloalkyl), $R^1$ and $R^2$, when taken together, represent a 5- or 6-membered heterocyclic ring which may contain a sulphur or oxygen atom, are known as insecticides having high insecticidal activity and low toxicity to warm-blooded animals (Japanese Unexamined Patent Publication No. 48137/1975 and Belgian Pat. Nos. 890162 and 892302). The aminosulfenylcarbamate derivatives of the formula (I) were developed to overcome the drawback of an insecticidal carbamate having high toxicity to warm-blooded animals. While the compound (I) is prepared by converting the carbamate to an aminosulfenylcarbamate, it is difficult to achieve this object if the unreacted carbamate remaining in the reaction mixture in a large amount is not removed from the reaction mixture to give the compound (I) having a high purity. To solve this problem, attempts have been made to purify the compound (I) to a high purity by removing the unreacted carbamate from the reaction mixture. For example, purification by distillation may be considered feasible in view of the compound (I) being oily, but the distillation of the compound (I) is impossible since the compound (I) has a high boiling point and decomposes at high temperatures. Generally the compounds (I) have been heretofore purified by silica gel column chromatography or by utilizing the difference in solubility in a solvent between the compound (I) and carbamate. However, the purification by silica gel column chromatography is commercially unfavorable. And the method utilizing the difference in a solvent usually involves the steps of dissolving the reaction mixture containing the unreacted carbamate in a solvent such as n-hexane in which an aminosulfenylcarbamate is easily soluble and a carbamate is sparingly soluble; crystallizing the unreacted carbamate; separating the aminosulphenylcarbamate from the crystal; and purifying the same. This method fails to achieve satisfactory purification and results in manufacture of the compound (I) of low purity because a small amount of the unreacted carbamate is dissolved in n-hexane.

It is an object of the present invention to provide a process for purifying the compound (I) to a high purity.

It is another object of the invention to provide a commercially favored process for purifying the compound (I).

Other features of the invention will become apparent from the following description.

According to the process of this invention, the compound (I) containing the unreacted carbamate is dissolved in an organic solvent which is insoluble in water and the solution is brought into contact with an aqueous alkali solution or a mixture of alkali, water and a water-soluble organic solvent. When the reaction mixture comprising the compound (I) and the unreacted carbamate is dissolved in a water-insoluble organic solvent according to the present invention, the unreacted carbamate may be deposited as a crystal depending on the selection of the solvent. In that case, the alkali treatment can be conducted after or without the removal of the crystal.

Useful water-insoluble organic solvents include those as mixed in the reaction system in conversion of the carbamate to the compound (I). Alternatively other class of solvent can be incorporated after removal of the solvent present in the reaction system. Suitable water-insoluble organic solvents can be any of conventional solvents which do not adversely affect the compound (I) nor decompose upon contact with the aqueous alkali solution. Exemplary of water-insoluble solvents are n-pentane, n-hexane, n-heptane, cyclohexane and like aliphatic hydrocarbons; diethyl ether, dipropyl ether, dibutyl ether and like ethers; dichloromethane, dichloroethane and like halogenated hydrocarbons; benzene, toluene, xylene, chlorobenzene and like aromatic hydrocarbons; etc. There is no specific limitation as to the amount of the compound (I) containing the unreacted carbamate and dissolved in the water-insoluble organic solvent and, accordingly, the amount thereof can be adequately selected from a wide range. The compound (I) is dissolved in the water-insoluble organic solvent in an amount of usually about 5 to about 80 w/v %, preferably about 10 to about 50 w/v % relative to the water-insoluble solvent. The amount of the unreacted carbamate present in the compound (I) is not particularly limited and it is present therein in an amount of usually about 2 to about 20 wt %, relative to the compound (I).

Useful water-soluble organic solvents include a wide variety of those heretofore known, such as methanol, ethanol and like alcohols; acetone, methyl ethyl ketone and like ketones; dioxane and like ethers; etc. Exemplary of useful alkalis are sodium hydrogencarbonate, potassium hydrogencarbonate and like alkali metal hydrogencarbonates; sodium carbonate, potassium carbonate and like alkali metal carbonates; sodium hydroxide, potassium hydroxide and like alkali metal hydroxides; etc. among which sodium hydroxide and potassium hydroxide are preferred. The concentration of alkali ranges usually from about 0.5 to about 20 wt %, preferably about 1 to about 10 wt % relative to the alkali solution or alkaline mixture (i.e. mixture of alkali, water and a water-soluble organic solvent). The ratio between the water and the water-soluble organic solvent is not particularly limited and can be suitably determined over a wide range. The amount of the water-soluble organic solvent is usually less than about 30% based on the total amount of the water and water-soluble organic solvent. The amount of the alkali solution or alkaline mixture to be contacted with the solution of the compound (I) in the water-insoluble solvent is variable with the amount of the carbamate and other conditions and can not be narrowly specified. The alkali solution or alkaline mixture is employed in an amount of usually about 0.01 to about 1.0 part, preferably about 0.1 to about 0.5 part per part of the solution of the compound (I). After contacting the solution of the compound (I) with the alkali solution or alkaline mixture, the reaction mixture is stirred at usually about −10° to about 50° C., preferably about 10° to about 30° C. for about 10 minutes to about 2 hours.

The alkali treatment of the compound (I) in the foregoing manner leaves little or no unreacted carbamate, consequently resulting in the increase in the purity of the compound (I) in the range of 92 to 98%. The compounds (I) purified by conventional methods have blackish brown color and are prone to reduced thermal or storage stability, whereas the alkali-treated compound (I) is discolored to reddish brown and exhibits improved thermal and storage stability. The purification process of this invention is, therefore, significantly advantageous in commercial manufacture.

The present invention will be described below in more detail with reference to the following Examples and Comparison Example.

EXAMPLE 1

Purification of 2,3-dihydro-2,2-dimethylbenzofuran-7-yl N-(N-isopropyl-N-ethoxycarbonylethylaminosulfenyl)-N-methylcarbamate Dissolved in 1 l of 1,2-dichloroethane was 479 g of 2,3-dihydro-2,2-dimethylbenzofuran-7-yl N-(N-isopropyl-N-ethoxycarbonylethylaminosulfenyl)-N-methylcarbamate having a purity of 85.6% and containing 3.5% 2,3-dihydro-2,2-dimethylbenzofuran-7-yl N-methylcarbamate. To the solution was added 400 ml of 1N-NaOH and the mixture was stirred at room temperature for 1 hour. Thereafter, the 1,2-dichloroethane layer was washed with water and separated. The 1,2-dichloroethane was removed at reduced pressure to give 440 g of an oily product. The oily product was quantitatively determined by high-performance liquid chromatography. As a result, the 2,3-dihydro-2,2-dimethylbenzofuran-7-yl N-(N-isopropyl-N-ethoxycarbonylethylaminosulfenyl)-N-methylcarbamate was found to have a purity of 92.8% and 2,3-dihydro-2,2-dimethylbenzofuran-7-yl N-methylcarbamate was not detected.

EXAMPLE 2

Purification of 2,3-dihydro-2,2-dimethylbenzofuran-7-yl N-(N,N-dibutylaminosulfenyl)-N-methylcarbamate Dissolved in 1 l of n-hexane was 434 g of 2,3-dihydro-2,2-dimethylbenzofuran-7-yl N-(N,N-dibutylaminosulfenyl)-N-methylcarbamate having a purity of 87.4% and containing 3.9% 2,3-dihydro-2,2-dimethylbenzofuran-7-yl N-methylcarbamate. To the solution was added 400 ml of 1N-NaOH and the mixture was stirred at room temperature for 1 hour. Thereafter the n-hexane layer was washed with water and separated and the separated layer was dried. The n-hexane was removed at reduced pressure to give 408 g of an oily product. The oily product was quantitatively determined by high-performance liquid chromatography. As a result, the 2,3-dihydro-2,2-dimethylbenzofuran-7-yl N-(N,N-dibutylaminosulfenyl)-N-methylcarbamate was found to have a purity of 93.1% and 2,3-dihydro-2,2-dimethylbenzofuran-7-yl N-methylcarbamate was not detected.

EXAMPLE 3

Purification of S-methyl N-[[N-methyl-N-(N-isobutyl-N-ethoxycarbonylethylaminosulfenyl)carbamoyl]oxy]thioacetimidate Dissolved in 1 l of 1,2-dichloroethane was 421 g of S-methyl N-[[N-methyl-N-(N-isobutyl-N-ethoxycarbonylethylaminosulfenyl)carbamoyl]oxy]thioacetimidate having a purity of 86.7% and containing 4.8% S-methyl N-[(methylcarbamoyl)oxy]thioacetimidate. To the solution was added 300 ml of 1N-NaOH and the mixture was stirred at room temperature for 20 minutes. Thereafter the 1,2-dichloroethane layer was washed with water and separated and the 1,2-dichloroethane was removed at reduced pressure to give 396 g of an oily product. The oily product was quantitatively determined by high-performance liquid chromatography. As a result, the S-methyl N-[[N-methyl-N-(N-isobutyl-N-ethoxycarbonylethylaminosulfenyl)carbamoyl]oxy]thioacetimidate was found to have a purity of 92.1% and S-methyl N-[(methylcarbamoyl)oxy]thioacetimidate was not detected.

EXAMPLE 4

Purification of S-methyl N-[[N-methyl-N-(N-benzyl-N-ethoxycarbonylethylaminosulfenyl)carbamoyl]oxy]thioacetimidate Dissolved in 1 l of 1,2-dichloroethane was 452 g of S-methyl N-[[N-methyl-N-(N-benzyl-N-ethoxycarbonylethylaminosulfenyl)carbamoyl]oxy]thioacetimidate having a purity of 88.2% and containing 4.2% S-methyl N-[(methylcarbamoyl)oxy]thioacetimidate. To the solution was added 300 ml of 1N-NaOH and the mixture was stirred at room temperature for 20 minutes. The 1,2-dichloroethane layer was washed with water and separated and the 1,2-dichloroethane was removed at reduced pressure to provide 423 g of an oily product. The oily product was quantitatively determined by high-performance liquid chromatography with the result that the S-methyl N-[[N-methyl-N-(N-benzyl-N-ethoxycarbonylethylaminosulfenyl)carbamoyl]oxy]thioacetimidate was found to have a purity of 94.3% and that S-methyl N-[(methylcarbamoyl)oxy]thioacetimidate Ewas not detected.

COMPARISON EXAMPLE

Purification of 2,3-dihydro-2,2-dimethylbenzofuran-7-yl N-(N-isopropyl-N-ethoxycarbonylethylaminosulfenyl)-N-methylcarbamate A 2 l quantity of n-hexane was added to 479 g of 2,3-dihydro-2,2-dimethylbenzofuran-7-yl N-(N-isopropyl-N-ethoxycarbonylethylaminosulfenyl)N-methylcarbamate having a purity of 85.6% and containing 3.5% 2,3-dihydro-2,2-dimethylbenzofuran-7-yl N-methylcarbamate. The mixture was stirred at 10° C. for 3 hours. Small amounts each of oils and crystals were settled in the resulting solution. Magnesium sulfate was added to adsorb the settled oils and the solution was filtered. The n-hexane was removed at reduced pressure from the filtrate to afford 452 g of an oily product. The oily product was quantitatively determined by high-performance liquid chromatography to find that the 2,3-dihydro-2,2-dimethylbenzofuran-7-yl N-(N-isopropyl-N-ethoxycarbonylethylaminosulfenyl)N-methylcarbamate had a purity of 86.3% and that 1.4% 2,3-dihydro-2,2-dimethylbenzofuran-7-yl N-methylcarbamate was detected. Thermal stability test Before and after alkali treatment, the compounds (I) obtained above were checked for thermal stability. The thermal stability test was conducted by placing an oily compound (I) in a constant temperature bath at 60° C. and measuring the decomposition ratio of the compound (I) after specific time intervals. Table I below shows the results.

TABLE I

| Compound (I) | Decomposition After 15 Days (%) | | Decomposition After 30 Days (%) | |
|---|---|---|---|---|
| | Before treatment | After treatment | Before treatment | After treatment |
| Example 1 | 6.5 | 2.1 | 16.3 | 5.9 |
| Example 2 | 6.1 | 1.8 | 14.2 | 4.7 |
| Example 3 | 5.3 | 1.2 | 11.4 | 4.1 |
| Example 4 | 4.2 | 1.3 | 12.5 | 3.8 |
| Comp. Ex. | 6.5 | 4.8 | 16.3 | 11.4 |

I claim:

1. A process for purifying an aminosulfenylcarbamate derivative represented by the formula (I)

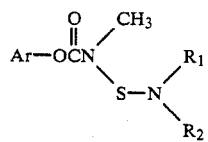  [I]

wherein Ar is

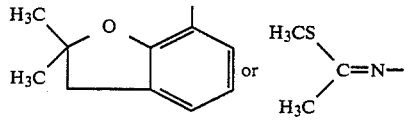

and $R^1$ and $R^2$ are the same or different and are each $C_{1-8}$ alkyl, $C_{3-6}$ cycloalkyl, benzyl which is unsubstituted or substituted with halogen, $C_{1-3}$ alkyl or $C_{1-3}$ alkoxy, phenyl which is unsubstituted or substituted with halogen, $C_{1-3}$ alkyl or $C_{1-3}$ alkoxy, —X—COOR$^3$ or —Y—CN (in which X and Y are each straight-chain or branched-chain alkylene and $R^3$ is $C_{1-8}$ alkyl or $C_{3-6}$ cycloalkyl), $R^1$ and $R^2$, when taken together, represent a 5- or 6-membered heterocyclic ring which may contain a sulphur or oxygen atom, the process comprising bringing a solution of the unreacted carbamate-containing aminosulfenylcarbamate derivative of the formula (I) in a water-insoluble organic solvent into contact with an aqueous alkali solution or a mixture of alkali, water and a water-soluble organic solvent.

2. A process as defined in claim 1 in which the compound of the formula (I) is that wherein Ar is

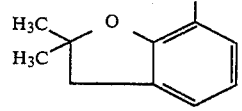

$R^1$ is —CH$_2$CH$_2$COOC$_2$H$_5$ and $R^2$ is isopropyl.

3. A process as defined in claim 1 in which the compound of the formula (I) is that wherein Ar is

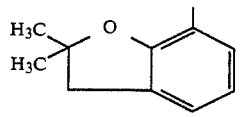

and $R^1$ and $R^2$ are both n-butyl.

4. A process as defined in claim 1 in which the compound of the formula (I) is that wherein Ar is

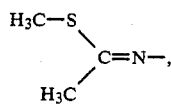

$R^1$ is —CH$_2$CH$_2$COOC$_2$H$_5$ and $R^2$ is benzyl.

5. A process as defined in claim 1 in which the compound of the formula (I) is that wherein Ar is

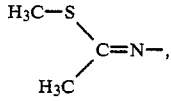

$R^1$ is —CH$_2$CH$_2$COOC$_2$H$_5$ and $R^2$ is isobutyl.

6. A process as defined in any one of claims 1 to 5 in which the alkali is sodium hydroxide or potassium hydroxide.

7. A process as defined in claim 6 in which the concentration of the alkali is about 0.5 to about 20% by weight based on the alkali solution or alkaline mixture.

* * * * *

UNITED STATES PATENT AND TRADEMARK OFFICE
CERTIFICATE OF CORRECTION

PATENT NO. : 4,532,339
DATED    : July 30, 1985
INVENTOR(S) : HISASHI TAKAO

It is certified that error appears in the above-identified patent and that said Letters Patent is hereby corrected as shown below:

On the cover page, after "Item [22]" insert

--- [30]      Foreign Application Priority Data

March 11, 1983     Japan................ 41185/1983 ---.

Signed and Sealed this

First Day of October 1985

[SEAL]

Attest:

DONALD J. QUIGG

Attesting Officer

Commissioner of Patents and
Trademarks—Designate